United States Patent [19]

Kiely

[11] Patent Number: 5,478,374
[45] Date of Patent: Dec. 26, 1995

[54] CARBOHYDRATE ACID AMIDE PLANT FERTILIZERS

[76] Inventor: Donald E. Kiely, 2521 Chatwood Rd., Birmingham, Ala. 35226

[21] Appl. No.: 253,918

[22] Filed: Jun. 3, 1994

Related U.S. Application Data

[63] Continuation-in-part of Ser. No. 928,007, Aug. 12, 1992, Pat. No. 5,329,044.

[51] Int. Cl.$^6$ .......................... C05F 11/00; C07C 229/00; C08G 4/00
[52] U.S. Cl. ................... 71/27; 528/230; 562/564; 562/556
[58] Field of Search .................. 71/27; 528/230; 562/564, 556

[56] References Cited

U.S. PATENT DOCUMENTS 4,833,230  5/1989  Kiely et al. ............................ 528/230
5,329,044  7/1994  Kiely et al. ............................ 562/564

OTHER PUBLICATIONS

Kane, Dissertation, U of Alabama Birmingham pp. 1, 39–41 (1992).
Hauck, "Slow–Release and Bioinhibitor—Amended Nitrogen Fertilizers" from Fertilizer Technology and Use, 3rd Ed., Soil Science Society of America (1985), pp. 293–322.
Kiely et al., *J. Carbohydrate Chem.*, 5(2), 183–7 (1986).
Schneider et al., *Tenside*, 4, No. 10, 330–4 (1967).

*Primary Examiner*—Ferris Lander
*Attorney, Agent, or Firm*—Stephen Gates; Glenna Hendricks

[57] ABSTRACT

The nitrogen in amides of aldonic and aldaric acids having 5 or 6 carbon atoms in the carbohydrate residue is available to support plant growth, i.e. the materials act as nitrogen fertilizers.

5 Claims, No Drawings

CARBOHYDRATE ACID AMIDE PLANT FERTILIZERS

This application is a continuation-in-part of U.S. patent application Ser. No. 07/928,007, filed Aug. 12, 1992, now U.S. Pat. No. 5,329,044.

FIELD OF THE INVENTION

This invention describes the use of a variety of synthetic carbohydrate acid amides as nitrogen plant fertilizers or fertilizer components.

BACKGROUND OF THE INVENTION

Nitrogen fertilizers are available in a myriad of forms.

In general they can be differentiated into simple water-soluble molecules which are essentially immediately available to plants, such as ammonia and nitrates, and those which exhibit a more or less controlled rate of dissolution (availability). R. D. Nauck in "Slow-Release and Bioinihibitor-Amended Nitrogen Fertilizers", in *USA Fertilizer Technology and Use* (3rd Edition), Soil Science Society of America, 677 South Segoe Road, Madison, Wisc. 53711 at page 293 states "One approach to increasing the efficiency of N fertilizer use by plants is to control the rate of N-fertilizer dissolution. This can be done by (i) developing compounds with limited water solubility and (ii) modifying water-soluble materials to delay release of their contained N to the soil solution."

Carbohydrate acid amides are known compounds and polymers which may be prepared by a number of methods. Preparation of gluconamides and glucaramides are described in D. E. Kiely, J. L. Navia, L. Miller and T-H. Lin, *J. Carbohydr. Chem.*, 5, 183 (1986) and references therein. Preparation of N-alkylglucaramides is described in F. Schneider and H-U. Geyer, *Tenside*, 4, No 10, 330 (1967). Methods for preparing N,N'-dialkylglucaramides may be found in R. W. Kane, Ph.D. dissertation, University of Alabama at Birmingham, 1992 and references therein. The preparations of additional N,N'-dialkylaldaramides are also described in that reference. Preparation of poly(alkylene aldaramides) is disclosed in Kiely and Lin, U.S. Pat. No. 4,833,230, May 25, 1989. Preparation of poly(heteroalkylene aldaramides), polyamides of aldaric acids, in particular glucaric acid, in which heteroatoms, such as nitrogen or oxygen, are connecting atoms in the alkylenediamine chain, are disclosed in copending U.S. patent applications Ser. No.07/927,913, Aug. 12, 1992 and Kiely et al., "Polyaldaramide Polymers Useful for Films and Adhesives", and "Charged Polyaldaramide Polymers", both filed May 24, 1994.

SUMMARY OF THE INVENTION

It has been found that the nitrogen in amides of aldonic and aldaric acids is available to support plant growth, i.e. the materials act as nitrogen fertilizers.

DETAILED DESCRIPTION OF THE INVENTION

It has been found that the growth of plants is enhanced by supplying nitrogen to a plant using as fertilizer a material comprising one or more compositions selected from the group consisting of the carbohydrate acid amides commonly known as aldonamides and aldaramides, which have 5 or 6 carbon atoms in the carbohydrate residue, preferably gluconamides and glucaramides. Glucaramides include monomeric glucaramides, polymeric poly(alkylene glucaramides) and poly(heteroalkylene glucaramides).

Aldonamides useful in the practice of the invention have the general formula:

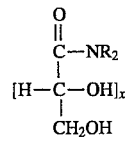

wherein each R is individually selected from the group consisting of hydrogen and alkyl having from 1 to about 16 carbon atoms and x is 3 or 4.

Aldaramides useful in the practice of the invention have the general formula:

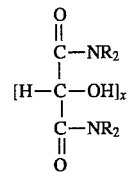

wherein each R is individually selected from the group consisting of hydrogen and alkyl having from 1 to about 16 carbon atoms and x is 3 or 4.

Polyaldaramides useful in the practice of the invention are polymers having the general formula:

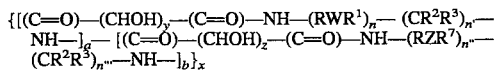

wherein y and z individually are 3 or 4;

a is an integer;

b may be zero or an integer;

n and n" individually may each be zero or an integer;

each individual R is selected individually from the group of divalent radicals consisting of alkylene, alkenylene, aryl- and alkyl-substituted alkylene and alkenylene, and $-R^4-$(arylene)$-R^{4-}$, $-R^4-$(alkyl- and alkenyl-substituted arylene)$-R^4-$ where each $R^4$ individually is alkylene having from 1–4 carbon atoms;

each individual $R^1$ and each individual $R^7$ is selected individually from the group consisting of R or a valence bond;

each individual $R^2$ and $R^3$ is selected individually from the group consisting of hydrogen, alkyl, alkenyl, alkynyl, aryl, aryl-substituted alkyl and alkenyl, and alkyl- and alkenyl-substituted aryl;

each individual n' may individually be zero or an integer with the proviso that when $R^1$ is a valence bond or n is zero n' must be at least two;

each individual n''' may individually be zero or an integer with the proviso that when $R^7$ is a valence bond or n" is zero n''' must be at least two;

each individual W and each individual Z is selected individually from the group consisting of consisting of $-Y-$, $-O-$, $-S-$, $-NR^5-$, $-PR^5-$, $-N^\oplus R^5R^6X^-$ and $-P^\oplus R^5R^6X^-$, wherein each individual $R^5$ is selected individually from the group consisting of alkyl, substituted alkyl, alkenyl, aryl, aralkyl and alkaryl and each individual $R^6$ is selected individually from the group consisting of hydrogen, alkyl, substituted alkyl, alkenyl and aralkyl and X is the anion of a salt-forming acid; and x is a number between about 10 and about 1,000.

A positive biological response from synthetic carbohydrate acid amides as the only source of nitrogen for plant growth has been determined using *Brassica rapa*. Some aldonamides and aldaramides are water soluble, others water insoluble. Positive biological results were obtained using both water soluble and water insoluble carbohydrate acid amides; thus all are useful as nitrogen fertilizers. The strongest biological responses were from the more water soluble materials. The film forming, water-soluble and the water-insoluble poly(glucaramides) also gave positive biological responses. These compositions may be used as specialty fertilizers per se, or in the case of film-forming polymers, as nitrogen releasing coating compositions or in coating compositions for water soluble nitrogen such as urea, to make time release nitrogen fertilizers. The aldaramide polymers may be used as nitrogen delivering materials for matrixes and encapsulation materials for water soluble nitrogen sources such as urea. The differing solubilities and solution rates of the aldonamides, aldaramides and particularly of the various poly(aldaramides) thus allows preparation of time-release fertilizers having a broad spectrum of release times.

The route by which nitrogen from these amides in soil becomes available to plants is not known to the applicants. Whatever the mechanism for nitrogen delivery to the plants, it is clear that the use of synthetic carbohydrate amides provides a wide range of materials capable of acting as nitrogen sources for plants, water soluble, water insoluble, film forming, charged and uncharged, based upon the broad technology available for making carbohydrate acid amides. In addition to use as fertilizers per se, uses include their use as fertilizer coatings, encapsulating agents, or matrixes to change the rate of release of other water soluble forms of nitrogen (e.g., urea) into the soil for plant utilization and as specialty valued added fertilizers for specific applications, for example as time release fertilizers. Because it is convenient to make a whole range of aldonamides, aldaramides, and polymeric alkylene and heteroalkylene copolymer aldaramides from one or more diamines and/or one or more aldaric acids, a whole range of such carbohydrate acid amides may be prepared by routine manipulation to obtain a wide range of water solubility and water insolubility properties, solid and film-forming properties and nitrogen delivering properties useful as nitrogen fertilizers or components of nitrogen fertilizers. The carbohydrate acid amides described are most economically derived from naturally occurring sugars, in particular glucose (D-glucose) because of its considerable commercial availability and low cost. Other carbohydrate acid amides from naturally occurring and available xylose, galactose and mannose also may be used in the applications described herein.

Experimental

Amides:

The carbohydrate acid amides tested as plant fertilizers were the following: 1) gluconamide, 2) glucaramide, 3) N-alkylgluconamides, 4) N,N'-dialkylglucaramides, 5) poly(alkylene glucaramides) and 6) poly(heteroalkylene glucaramides). All of the gluconamides and glucaramides employed were of the D-configuration as they were derived from the naturally occurring form of glucose, D-glucose.

Plants:

The growth and development of Wisconsin Fast Plant™ *Brassica rapa* was used to evaluate the availability of nitrogen (N) from the above mentioned carbohydrate acid amides when applied to a potting mix. Wisconsin Fast Plant™ *Brassica rapa* is a rapid-cycling plant that completes its life cycle in an average of 35 days. Fourteen days after planting seeds of these genetically selected rapid-cycling brassicas the initial flowers will be produced at an average plant height of 13 cm. Flowers pollinated (by manual transfer of pollen to the stigmas with a brush) are fertilized within 24 hours and pods (siliques) visibly swell 3 to 5 days after pollination. In these experiments, after flowering began plants were pollinated every other day until the development of new flowers ceased.

Culture System:

A static, unaerated solution culture system was used to provide nutrient solution by capillary action to *Brassica rapa*. The solution reservoir for each experimental treatment consisted of a six ounce Styrofoam® cup fitted with a plastic cover in which a 1 cm slit was cut out on an edge to accommodate a water mat strip. A 4.8 cm× 9 cm strip of water mat material was first soaked in a liter of water to which a milliliter of liquid detergent was added. The water was then squeezed out of the mat. The mat was soaked and squeezed twice more. After soaking the mat once more, an end of it was laid onto the surface of the cup cover with the remainder extended through the slit cap and into the cup. The wetted mat provided a continuous source of nutrient solution containing dissolved water soluble amides, or water, in the cases where water insoluble amides were tested, to the developing plants by providing a capillary path from the solution in the cup to the wicks extending from the planting quads (see below).

Planting Unit:

A four-sectioned, Styrofoam® container or "quad" accommodated the planting mix and seeds. The quad was 4.8 cm× 4.8 cm× 4.4 cm deep and each of the four cells has a 2 cm square opening at the top, tapered to 0.5 cm square opening at the bottom. A trapezoidal wick (5 cm long; 1 cm wide in middle and tapered to a point on each end) was inserted one-half its length through the 0.5 cm opening at the bottom of each of cell.

Planting Mix:

A soilless mix consisting of ⅔ milled peat moss and ⅓ fine vermiculite was combined with a loam soil in a 3:1 ratio (v/v). The complete mix was carefully added up to the top of each cell, insuring that the wick extended upwardly along the inside wall of the cell. Water insoluble amides were mixed directly with the planting medium. Water soluble amides were dissolved in the aqueous nutrient solution.

Planting Procedure:

Two seeds were added to a 4 mm depression in the potting mix in each cell. The seeds were covered with just enough potting mix so they were no longer visible. Nutrient solution corresponding to the composition of that in the cup reservoir for a specific experimental treatment was then gently added from above with a pipet to saturate the planting mix and then for each of the first 3 days to insure adequate moisture during germination of the seeds. In those cells in which both seeds germinated, the youngest was pulled from each cell four or five days after planting.

Nutrient Solutions:

One-fourth strength Hoagland's complete nutrient solution (D. R. Hoagland and D. I. Arnon, *California Agricultural Experiment Station Circular* 347, University of California, Berkeley, Calif.) served as the control (plus N) nutrient solution. One-fourth strength Hoagland's solution formulated without N was the basal solution to which specific water soluble carbohydrate acid amines were added to evaluate availability of N from the amides. This basal solution served as the minus N control solution. Initially, 100 mL of nutrient solution were added to the cup reservoir and the cup marked for that volume. The volume was readjusted to the 100 mL mark every five days. Deionized water was used the first time to adjust the volume. Subsequently, the nutrient solution (specific one being evaluated) or deionized water was alternately added after each successive five days.

Measurement of Biological Response:

The relationship between the number of pods per plant and available nitrogen, phosphorus, and potassium is almost linear (P. H. Williams, *Wisconsin Fast Plants*™ *Manual*, Carolina Biological Supply, Burlington, North Carolina). This conversion of increased nutrient concentration into increased reproductive output was used as a bioassay to evaluate the availability of nitrogen supplied by specific carbohydrate acid amides. Forty days after planting, the number of pods was determined for each plant in a quad and an average number of pods determined from the four plants per treatment.

Results:

In the absence of any nitrogen added to the nutrient solution, an average of about two pods per plant developed, whereas about 29 pods per plant developed when complete Hoagland's solution was provided. As can be seen in Tables 1 and 2, the number of pods supported per plant by different individual carbohydrate acid amides tested as sources of nitrogen was variable.

TABLE 1

Seed pods formed by *Brassica rapa* in response to monomeric nitrogen sources

| Nitrogen Source[1] | Average Number of Pods per Plant[2] |
|---|---|
| control, minus nitrogen | 3.00 |
| control + nitrogen ($NO_3^-$; complete Hoagland's) | 17.50 |
| gluconolactone | 2.67 |
| gluconamide | 7.50 |
| N-butylgluconamide | 9.00 |
| N-dodecylgluconamide | 3.50 |
| methyl glucarate-1,4-lactone | 2.50 |
| glucaramide | 12.00 |
| N,N'-dibutylglucaramide | 3.75 |
| N,N'-dihexylglucaramide | 9.75 |
| N,N'-didodecylglucaramide | 1.33 |

[1]one-fourth strength Hoagland's nutrient solution formulated without nitrogen
[2]average yield from 3–4 plants Referring to Table 1, the first two entries are the −N and +N controls. The lack of nitrogen in the −N control results in a dramatic decrease in pod production. Next is water soluble gluconolactone, the C-1 carboxylic acid lactone derived from glucose. In aqueous solution the lactone is in equilibrium with the free acid form, gluconic acid. Gluconic acid contains no nitrogen and a biological response comparable to the −N control is observed.

The next three entries are amides of (monobasic) gluconic acid. Water soluble gluconamide, the parent 1° amide, gives a significant positive biological response as does a water soluble N-alkyl derivative of gluconamide, N-butylgluconamide. N-decylgluconamide, which is insoluble in water, gave a lesser positive biological response.

Water soluble methyl glucarate 1,4-lactone, a monomethyl ester/lactone of glucaric acid (an aldaric acid), the acyclic dicarboxylic acid derived from glucose. In aqueous solution the ester/lactone is hydrolyzed to glucaric acid. The ester/lactone or free acid forms of glucaric acid contain no nitrogen and a biological response comparable to the −N control is observed.

The remaining entries are derivatives of (dibasic) glucaric acid; glucaramide is water soluble and the following three N,N' substituted glucaramides water insoluble. Glucaramide, the parent bis-1° amide, gives a significant positive biological response as does N,N'-dihexylglucaramide. N,N'-dibutylglucaramide, also gives a positive biological response, although not as great as that from the dihexyl compound. N,N'-didodecylglucaramide is highly water insoluble however the seeds germinated and the plants lived, but did not grow well and exhibited reduced pod production.

TABLE 2

Seed pods formed by *Brassica rapa* in response to polymeric nitrogen sources.

| Nitrogen Source[1] | Average Number of Pods per Plant[2] |
|---|---|
| control, minus nitrogen | 2.33 |
| control, + nitrogen ($NO_3^-$; complete Hoagland's) | 28.75 |
| poly(hexamethylene glucaramide) | 4.50 |
| poly(tetramethylene glucaramide) | 9.00 |
| poly(tetramethylene glucaramide) (2X) | 18.00 |
| poly(4-methyl-4-azaheptamethylene glucaramide) | 4.75 |
| poly(3,6-dioxaoctamethylene glucaramide) | 3.67 |

[1]one-fourth strength Hoagland's nutrient solution formulated without nitrogen
[2]average yield from 3–4 plants Again, the first two entries and are the −N and +N controls.

The remaining entries are examples of poly(alkylene glucaramides). Poly(hexamethylene glucaramide) is an example of a water insoluble poly(alkylene glucaramide). The poly(tetramethylene glucaramide) entries represent two concentrations of the same water soluble poly(alkylene glucaramide), with the second entry double the concentration of entry the first. These results indicate the following: i. the water insoluble and water soluble polymers poly(alkylene glucaramides) give a positive biological response; ii. the water soluble poly(alkylene glucaramide) gives a greater biological response than does the water insoluble polymer; iii. doubling the concentration of the water soluble polymer approximately doubles the positive biological response.

The final two entries are examples of water soluble, film forming poly(heteroalkylene glucaramides), i.e., glucaric acid polyamides in which heteroatoms, such as oxygen or nitrogen, are connecting atoms in the alkylenediamine chain. Each of the entries, where nitrogen is the heteroatom and oxygen is the heteroatom, showed a positive biological response. The penultimate entry is a copolymer of 4-aza-4-methylheptamethylenediamine and glucaric acid. The last entry is a copolymer of 3,6-dioxaoctamethylenediamine and glucaric acid.

In summary, a positive biological response has been determined using synthetic carbohydrate acid amides as the only source of nitrogen for plant growth. Positive biological results were obtained using both water soluble and water insoluble carbohydrate acid amides; thus all are useful as nitrogen fertilizers. The strongest biological responses were from the more water soluble materials. Film forming, water-soluble and water-insoluble poly(glucaramides) also gave positive biological responses.

I claim:

1. A method of promoting plant growth which comprises supplying nitrogen to a plant as a fertilizer comprising one or more compositions selected from the group consisting of aldonamides and aldaramides having 5 or 6 carbon atoms in the carbohydrate residue.

2. The method of claim 1 in which the aldonamide is a gluconamide.

3. The method of claim 1 in which the aldaramide is a glucaramide.

4. The method of claim 1 in which the aldaramide is a poly(alkylene aldaramide) or a poly(heteroalkylene aldaramide).

5. The method of claim 4 in which the aldaramide is a poly(alkylene glucaramide) or a poly(heteroalkylene glucaramide).

* * * * *